United States Patent
Nakao et al.

(10) Patent No.: US 8,115,915 B2
(45) Date of Patent: *Feb. 14, 2012

(54) DEFECT INSPECTION METHOD AND APPARATUS

(75) Inventors: Toshiyuki Nakao, Yokohama (JP); Yoshimasa Oshima, Yokohama (JP); Yuta Urano, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/021,076

(22) Filed: Feb. 4, 2011

(65) Prior Publication Data

US 2011/0128534 A1  Jun. 2, 2011

Related U.S. Application Data (63) Continuation of application No. 12/713,500, filed on Feb. 26, 2010, now Pat. No. 7,916,288, which is a continuation of application No. 12/362,950, filed on Jan. 30, 2009, now Pat. No. 7,675,613.

(30) Foreign Application Priority Data

Feb. 1, 2008 (JP) ................. 2008-022255

(51) Int. Cl.
G01N 21/00 (2006.01)
(52) U.S. Cl. ................. 356/237.2; 356/237.4; 356/237.5
(58) Field of Classification Search .................. None
See application file for complete search history.

(56) References Cited

U.S. PATENT DOCUMENTS

| 6,081,325 | A | 6/2000 | Leslie et al. |
| 7,675,613 | B2* | 3/2010 | Nakao et al. ............... 356/237.2 |
| 7,787,115 | B2* | 8/2010 | Otani et al. ................ 356/237.3 |
| 7,881,520 | B2* | 2/2011 | Ueno et al. .................... 382/149 |
| 2007/0182958 | A1 | 8/2007 | Manabe et al. |
| 2008/0002194 | A1 | 1/2008 | Matsui |
| 2008/0144024 | A1 | 6/2008 | Nakano |
| 2008/0297783 | A1 | 12/2008 | Urano et al. |
| 2008/0304055 | A1 | 12/2008 | Oshima et al. |
| 2009/0279081 | A1 | 11/2009 | Urano et al. |

FOREIGN PATENT DOCUMENTS

| JP | 09-304289 | 11/1997 |
| JP | 2000-162141 | 6/2000 |

* cited by examiner

*Primary Examiner* — Gordon Stock, Jr.
(74) *Attorney, Agent, or Firm* — Antonelli, Terry, Stout & Kraus, LLP.

(57) ABSTRACT

A method and apparatus for inspecting a defect of a surface of a sample in which a laser beam is irradiated on a sample surface so that at least a part of an illumination field of the laser beam illuminates a first area of the sample surface, a plurality of scattered light rays from the first area caused by the irradiation in the irradiating is detected, errors of inclination of an illumination apparatus and a sensor for the plurality of scattered light rays detected are corrected, the plurality of scattered light rays corrected is at least one of added and averaged, a defect on the sample surface based on the plurality of scattered light rays in accordance with the correcting of errors of inclination of the illumination apparatus and the sensor is determined.

13 Claims, 11 Drawing Sheets

DEFECT INSPECTION METHOD AND APPARATUS

CROSS REFERENCE TO RELATED APPLICATION

This application is a continuation of U.S. Ser. No. 12/713,500, filed Feb. 26, 2010, now U.S. Pat. No. 7,916,288, which is a continuation of U.S. application Ser. No. 12/362,950, filed Jan. 30, 2009, now U.S. Pat. No. 7,675,613, the contents of which are incorporated herein by reference. The present application is related to U.S. application Ser. No. 12/109,548, filed Apr. 25, 2008 by some of the inventors herein, now U.S. Pat. No. 7,710,557.

INCORPORATION BY REFERENCE

The present application claims priority from Japanese Patent application No. 2008-022255 filed on Feb. 1, 2008, the contents of which is hereby incorporated by reference herein.

BACKGROUND

The present invention relates to a defect inspection method for inspecting a minute defect existing on a sample surface and a defect inspection apparatus therefor.

In production lines of semiconductor substrates, thin film substrates, etc., in order to maintain and improve the yield of a product, inspection of a defect that may exist on the surface of semiconductor substrates, thin film substrates, etc. is performed. As conventional technologies, JP-A-Hei9(1997)-304289 (patent document 1) and JP-A-2000-162141 (patent document 2) are known. In order to detect a minute defect, a laser beam focused to a few tens μm is irradiated thereon and scattered light from the defect is converged and detected.

In connection with rapid miniaturization of LSI wiring in recent years, the size of a defect that should be detected is approaching a detection limit of optical inspection. According to the semiconductor load map, mass production of LSI of a 36-nm node is going to be started in 2011, and a capability of detecting the defect having a size of about a half of DRAM ½ pitch is considered required. It is known that a magnitude I of scattered light occurring when the defect is illuminated by a laser has a relation of $I \propto d^6$, where d denotes a particle size of the defect. That is, when the defect size becomes small, the scattered light occurring thereby will decrease rapidly. Although, as methods of increasing the scattered light occurring, there exist wavelength shortening of illumination wavelength, power increasing of a laser, reduction of a laser illumination spot, etc., any of these methods comes with a possibility of giving damage to the sample due to an increase of temperature of an irradiated portion.

SUMMARY

An object of the present invention is to provide a defect inspection method and apparatus capable of inspecting a minute defect existing on a sample surface with high sensitivity while suppressing damage to the sample.

As a method of increasing the scattered light that is to be detected while suppressing temperature rise of an irradiated portion, considered is a method whereby approximately the same area is irradiated a plurality of times and a plurality of detected scattered light rays are added. However a plurality of scattered light rays from approximately the same area that are detected actually by this method may have errors of detection timings that arise from position shifts and angle shifts of an illumination apparatus, inclination of the sensor, etc. In such a case, it is considered that if the plurality of detected scattered light rays are added as they are, the scattered light rays cancel to one another, and consequently defect detection sensitivity falls. To solve this problem, the present application proposes a method for correcting detection timing errors that the plurality of scattered light rays have.

Representative aspects among aspects of the invention disclosed by the present invention will be explained briefly as follows:

(1) One of the aspects of the present invention is a defect inspection method of the sample surface, including: an irradiation step of irradiating a laser beam on a first area of the sample surface a plurality of times; a detection step of detecting a plurality of scattered light rays from the first area caused by the plurality of times of irradiation; a correction step of correcting the errors of the detection timings that the plurality of scattered light rays detected in the detection step have; a step of adding or averaging the plurality of scattered light rays corrected in the correction step; and a defect determination step of determining a defect on the sample surface based on a calculation result by the step of adding or averaging.

(2) An other of the aspects is the defect inspection method described in (1), wherein in the correction step, the correction is performed using a detection timing error value that is decided using a reference wafer having a reference point that is a defect whose position is known.

These features and advantages of the invention will be apparent from the following more particular description of preferred embodiments of the invention, as illustrated in the accompanying drawings.

DESCRIPTION OF THE PREFERRED EMBODIMENTS

Figure 1:
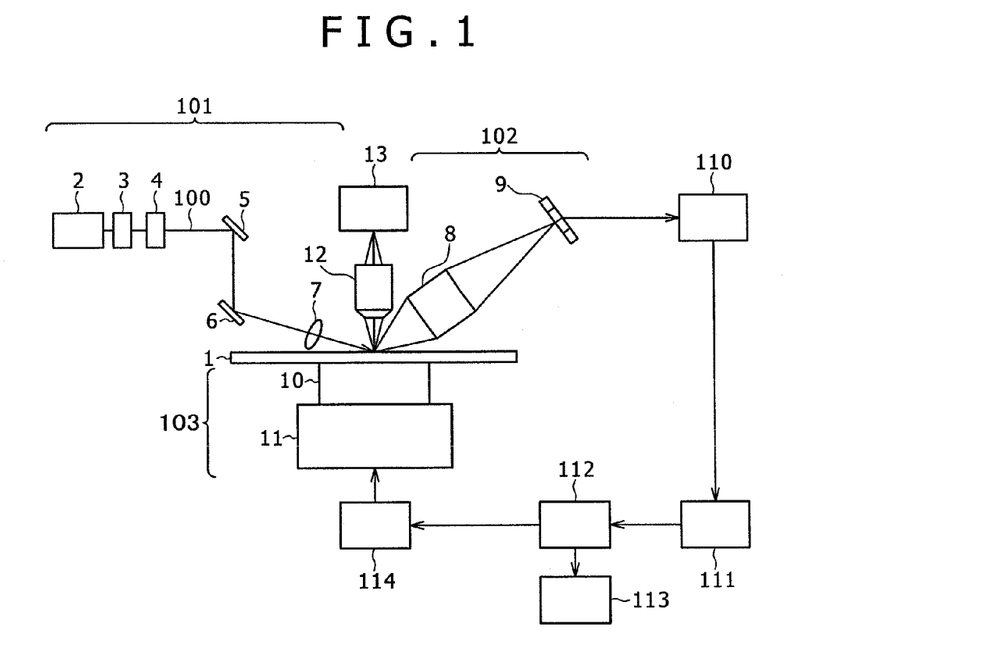
FIG. 1 is a first embodiment of a defect inspection apparatus according to the present invention.

One example of embodiments of a defect inspection apparatus according to the present invention will be explained using FIG. 1. The defect inspection apparatus shown by FIG. 1 is configured by having an illumination optical system 101, a detection optical system 102, a wafer stage 103, a circuit 110, and a signal processing section 111. The illumination optical system 101 is constructed using a laser light source 2, a beam expander 3, a homogenizer 4, mirrors 5, 6, and a collective lens 7. A laser beam 100 emitted from the laser light source 2 is adjusted in beam diameter by the beam expander 3 so that it may have a desired size, is converted by the homogenizer 4 so as to have a uniform illuminance distribution, and is made to conduct linear illumination in an area under inspection of a wafer 1 by the collective lens 7. Here, as the laser light source 2, what is necessary is just to use a laser light source oscillating an ultraviolet or vacuum ultraviolet laser beam. The beam expander 3 is an anamorphic optical system, and is constructed using a plurality of prisms. The beam expander 3 changes a beam diameter only in one direction in a plane perpendicular to the optical axis and conducts linear illumination on the sample using the collective lens. The irradiation may be conducted using a cylindrical lens, not with a combination of the collective lens 7 and the expander 3. When a single body of cylindrical lens is used, it is effective in a point that slimming of the optical system can be attained. Moreover, although the homogenizer 4 is used in order to make illumination intensity uniform, an illuminance distribution may be made uniform by using a diffraction optical element or fly eye lens, for example. Further, the illumination may be performed without using the homogenizer 4. Omission of the homogenizer makes it possible to suppress attenuation of the laser beam intensity and to conduct illumination at an intense illuminance.

Figure 2:
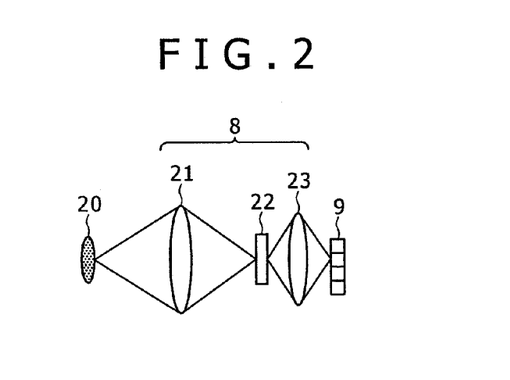
FIG. 2 is a detection optical system in the first embodiment of the defect inspection apparatus according to the present invention.

The detection optical system 102 is constructed by having an image formation system 8 and a photodiode array 9. The detection optical system 102 will be explained in detail using FIG. 2. The detection optical system 102 is constructed using a collective lens 21, an image intensifier 22, an image formation lens 23, and the photodiode array 9. Light rays scattered from an illumination field 20 are converged by the collective lens 21, and the scattered light rays are amplified by the image intensifier 22 and imaged onto the photodiode array 9 via the image formation lens 23. Here, although the image intensifier 22 is used in order to amplify the scattered light so that weak scattered light may become detectable, a sensor that has a high amplification ratio itself, for example, EM-CCD, a multi-anode PMT, etc. may be used, even without using the image intensifier. If any of these sensors is used, it will be effective in a point that slimming of the apparatus can be attained. In addition, the photodiode array 9 is used in order to receive the scattered light and perform photoelectric conversion on it. A TV camera, a CCD linear sensor, a TDI, the multi-anode PMT, a two-dimensional sensor, or the like may be used instead of it. It becomes possible to inspect a large area at once, for example, by using a two-dimensional sensor.

This photodiode array 9 generates an electric signal in proportional to the amount of received light. The electric signal generated by the photodiode array 9 undergoes necessary amplification, noise processing, and analog-to-digital conversion in the analog circuit 110. A plurality of optical signals that are of scattered light rays from approximately the same area are added and processed by defect determination in the signal processing section 111, and results lead to display of the defect map in a map output section 113 via a CPU 112. The wafer stage 103 is constructed with a chuck for holding the wafer 1 (not shown), a rotation stage 10 for rotating the wafer 1, and a translation stage 11 for moving the wafer 1 in a radial direction (one axis direction). The wafer stage 103 allows the whole sample surface to be illuminated spirally by conducting rotation scanning and translation scanning. A stage controller 114 controls rotational speed and translation speed so that a desired area may be able to be illuminated. An imaging optical system 12 and a CCD camera 13, which will be described later, are used to designate the rotation center of the wafer and to monitor an illumination position and an angle that a longitudinal direction of an illumination and a translation direction of the stage make.

Figure 3:
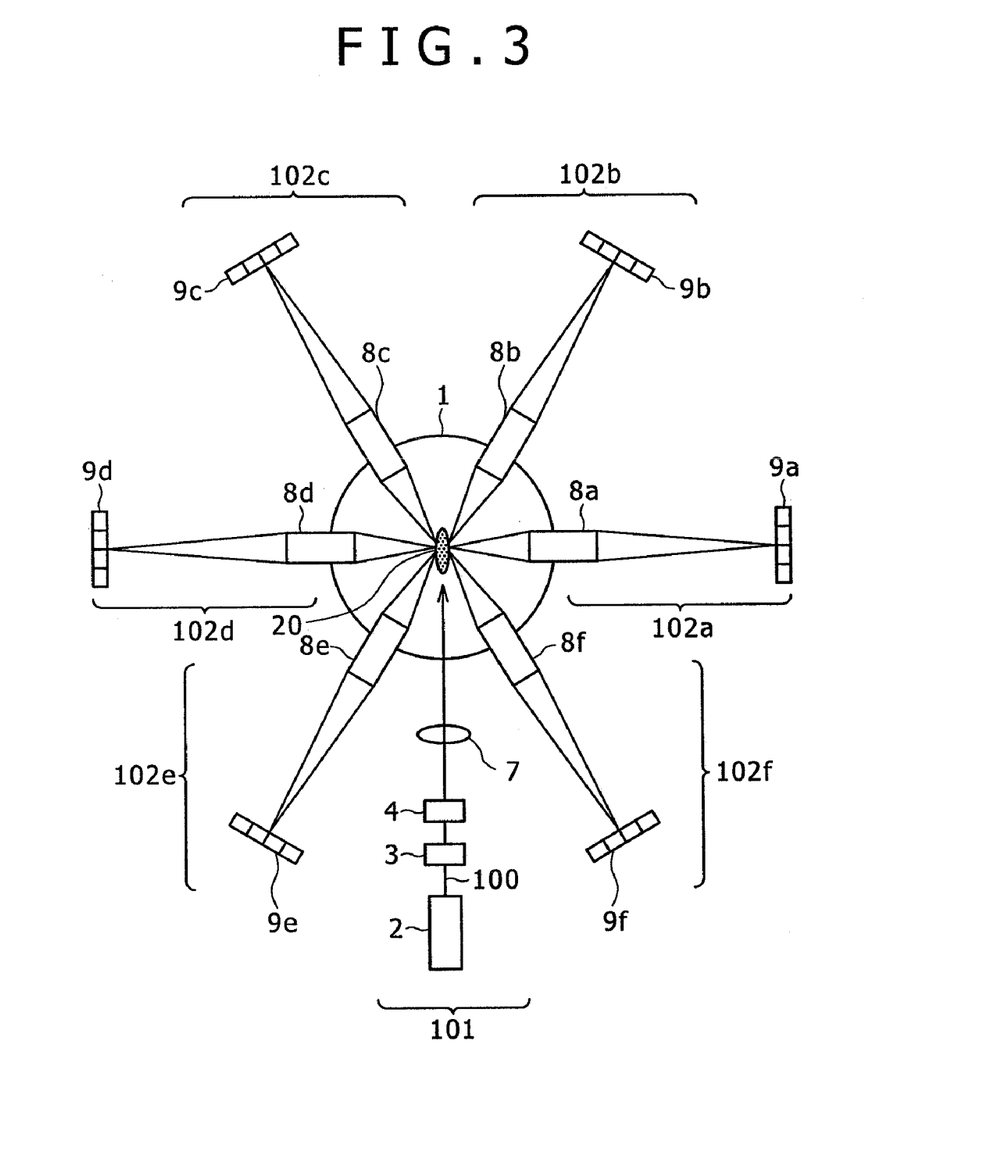
FIG. 3 is a top view of the first embodiment of the defect inspection apparatus according to the present invention.

Although the explanation was given in the example where one illumination optical system and one detection optical system are provided in FIG. 1, it is all right to adopt a configuration where a plurality of illumination optical systems and detection optical systems exist by properly combining a slant illumination optical system of conducting illumination from a low elevation angle to the sample, a vertical illumination optical system of conducting illumination from an approximately vertical direction to the sample, also a low-angle detection optical system of performing detection at a low elevation angle to the sample, and a high-angle detection optical system of performing detection at a higher elevation angle than that of the low-angle detection optical system to the sample. Making an annotation on the slant illumination optical system and the vertical illumination optical system, since the use of the slant illumination optical system can improve detection sensitivity and the use of the vertical illumination optical system can improve a classification capability of defects, any of the two may be used properly according to a use. Moreover, it becomes possible to improve accuracy of defect classification by using a combination of these illumination optical systems and/or detection optical systems. For example, for a convex defect, when illumination is conducted from a slant direction, large scattered light can be detected with the low-angle detection optical system; for a concave defect, when illumination is conducted from the vertical direction, large scattered light can be detected with the high-angle detection optical system. Moreover, if there exist a plurality of detection optical systems in different azimuth angle directions, as shown in FIG. 3, it poses no problem. That is, FIG. 3 is a diagram of one example embodiment of the defect inspection apparatus according to the present invention when viewed from a viewpoint above it, showing a wafer 1, the illumination optical system 101, and detection optical systems 102a to 102f. The detection optical systems 102a to 102f are constructed with image formation systems 8a to 8f and the photodiode arrays 9a to 9f, respectively. A detection signal undergoes necessary amplification, noise processing, and analog-to-digital conversion in the analog circuit. In the signal processing section, an addition operation and the defect determination are performed on a plurality of optical signals generated by scattering from approximately the same area, which will display the defect map in the map output section via the CPU (not shown). Here, explaining a configuration of the detection optical system, each of the image formation systems 8*a* to 8*f* is constructed with a collective lens, an image intensifier, and an imaging lens (not shown).

In this way, if the detection optical systems existing in a plurality of azimuth angles are used, in the case where angular characteristics of the scattered light rays occurring change due to the size and shape of a defect, a film kind of the sample, and surface roughness, the inspection can be performed by selecting a detection optical system that has small noise and is capable of detecting more of the scattered light rays from the defect; therefore, it becomes possible to improve the detection sensitivity. Regarding arrangement of the detection optical systems, although an example where six detection optical systems are arranged in different azimuth angle directions is shown in FIG. 3, the number of the detection optical systems does not necessarily need to be six and the azimuth angle directions in which they are arranged has no limitation, either. Moreover, the plurality of detection optical systems does not need to be arranged approximately in the same elevation angle, and it poses no problem that they are arranged in differ elevation angles. Further, detectors do not need to be arranged approximately in the same azimuth angle. In FIG. 3, although the laser illumination is conducted in a direction parallel to the longitudinal direction of the illumination, the longitudinal direction of the illumination and a direction in which the laser is irradiated do not need to be approximately the same, and the illumination may be performed from a different direction. By conducting the illumination from different directions, the scattered light distribution occurring due to a defect, such as COP and micro scratch, can be changed; therefore, classification performance can be improved by a combination of the detection signals of the detectors existing in a plurality of azimuth directions.

Figure 4:
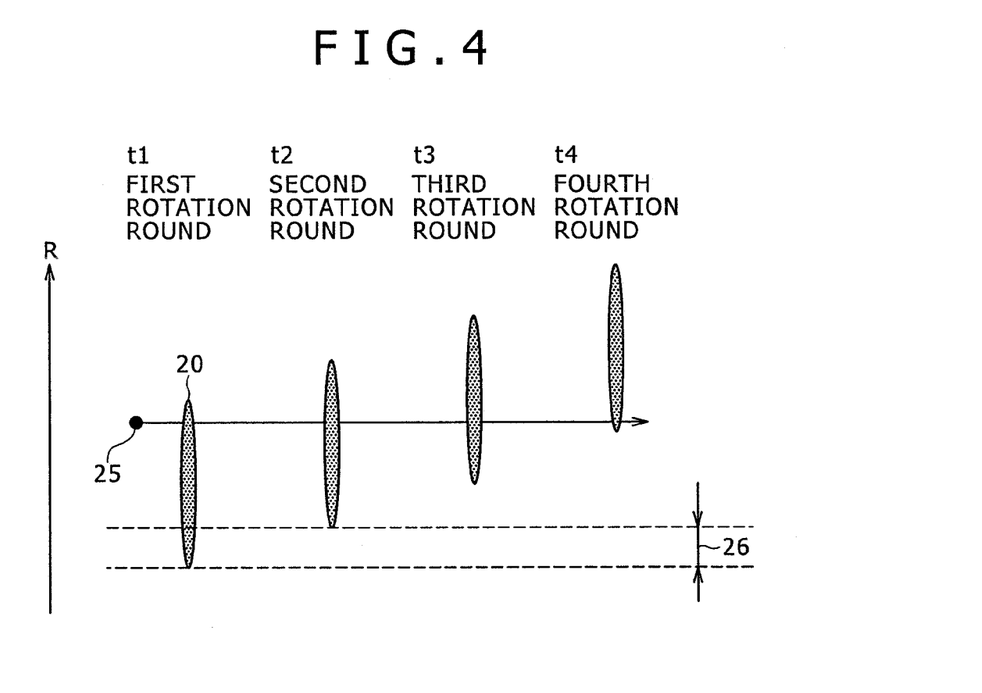
FIG. 4 is an explanatory diagram about a method for illuminating approximately the same area of a sample a plurality of times.

Next, a method for performing inspection with high sensitivity by irradiating approximately the same area of the sample surface a plurality of times while suppressing damage to the sample will be explained. The stage holding the sample is translating at an approximately constant speed in the radial direction (R direction) while making rotation. A distance that the stage makes in the radial direction at a time point of having made approximately one rotation is called a feed pitch. The whole sample surface is spirally scanned by performing rotation and translation. The present invention is characterized in that illumination is conducted on approximately the same area a plurality of times by setting the length of an illumination field to be longer than the feed pitch length. The inspection method will be explained in detail below. First, the method for illuminating approximately the same area of the sample a plurality of times will be explained using FIG. 4. FIG. 4 is an explanatory diagram of a case where the length of the illumination field 20 is four times a feed pitch 26, and the illumination is conducted to a defect 25 four times. If the first illumination is conducted to the defect 25 at time t1, the wafer makes approximately one rotation at time t2, the illumination field proceeds in the radial direction by a length of the feed pitch 26, and the defect 25 is illuminated again. After this, at time t3 and at time t4, the wafer makes approximately one rotation and allows the defect 25 to be illuminated. That is, in the case of FIG. 4, the defect 25 can be illuminated four times and the detected light undergoes addition processing in the analog circuit or signal processing section. By illuminating approximately the same area of the sample a plurality of times in this way, a minute defect existing on the sample surface can be inspected with high sensitivity without causing damage to the sample due to temperature rise of an irradiated portion. Incidentally, it is not necessary that the number of times of illumination is four times, and any times may be all right as long as the number expresses a plurality of times of illumination. Moreover, regarding the illumination optical system, not only a linear illumination may be generated using the beam expander and the cylindrical lens, but also a long illumination field may be generated by dividing the laser beam using a Wollaston prism and aligning the divided laser beams in the radial direction and illumination may be performed on the sample surface. Although a plurality of scattered light rays from approximately the same area are added and the defect detection is performed, at this time, the plurality of scattered light rays may be averaged, not being added, to perform the defect detection. Moreover, a distance between two illumination fields that were divided can be adjusted freely, and it poses no problem that illumination is conducted with beams overlapped or with the beams separated. By this adjustment, it becomes possible to adjust the number of times of illumination that will be done on approximately the same area. Furthermore, not only the divided laser beams may be aligned to conduct illumination from approximately the same direction, but also, for example, both the slant illumination optical system and the vertical illumination optical system may be used simultaneously to conduct illumination so that the two illumination fields may be arranged side by side to conduct illumination. By this simultaneous illumination, the same defect will be illuminated approximately from vertical and slant directions in a single inspection, which will lead to attainment of improved performance of defect classification by using a difference in detection elevation angle and in detection azimuth. Moreover, the illumination light does not need to be a linear illumination, and other illuminations, such as a spot illumination and an area illumination, can be used. If an illumination field length is longer than the pitch length, approximately the same area can be irradiated a plurality of times. Similarly, a deformed spot illumination like an elliptical illumination can irradiate approximately the same area a plurality of times provided that the illumination field length is longer than the feed pitch length.

Figure 5:
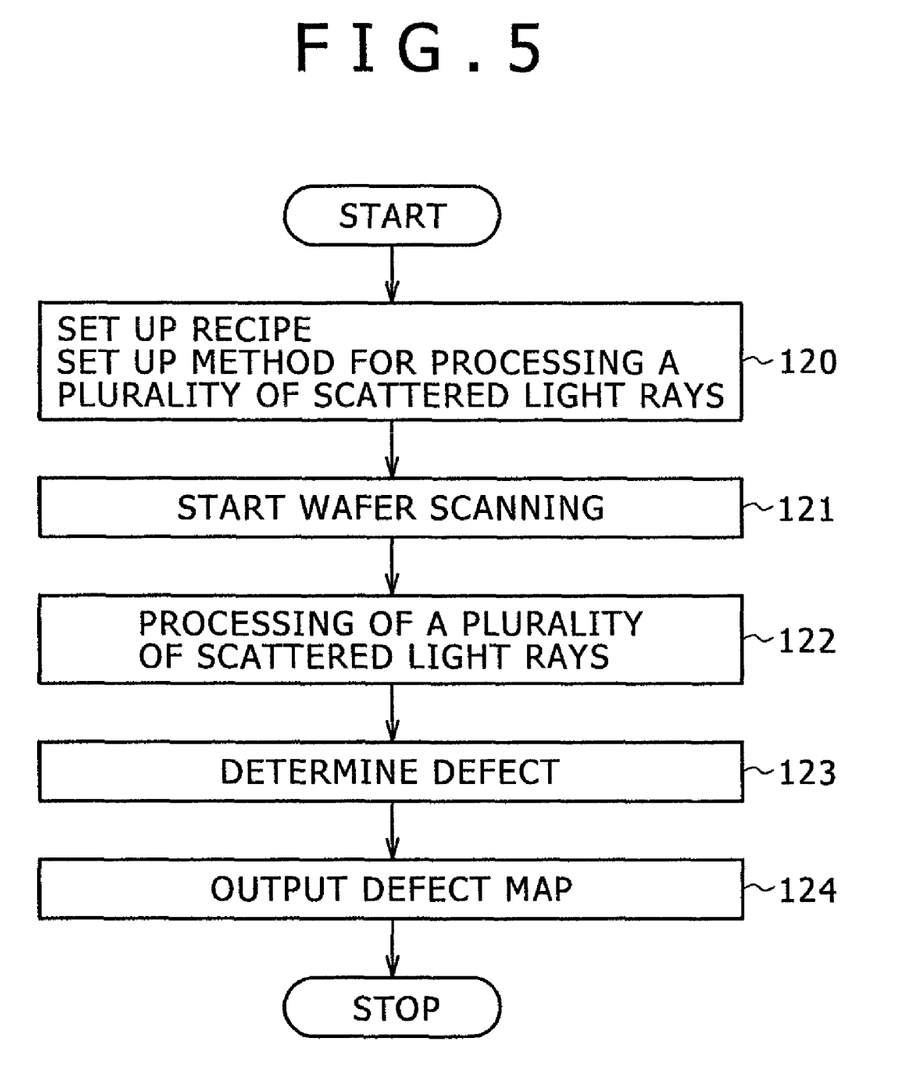
FIG. 5 is a defect detection processing flowchart showing a defect inspection method according to the present invention.

Next, a method for detecting a defect on the sample surface using the defect inspection apparatus will be explained using a defect detection processing flow of FIG. 5. First, by recipe setup, inspection conditions, such as an illumination direction and sensor sensitivity, are set up (Step 120). Setup of the length of the illumination field, the feed pitch, and the processing method that will be done to the scattered light are also included in it. Then, wafer scanning is started (Step 121) and signal processing of the plurality of scattering light rays being set up by the recipe setup is performed to detected scattered light (Step 122). Next, the defect determination is performed based on the signal that was processed (Step 123), and a defect map is outputted (Step 124).

Figure 6A:
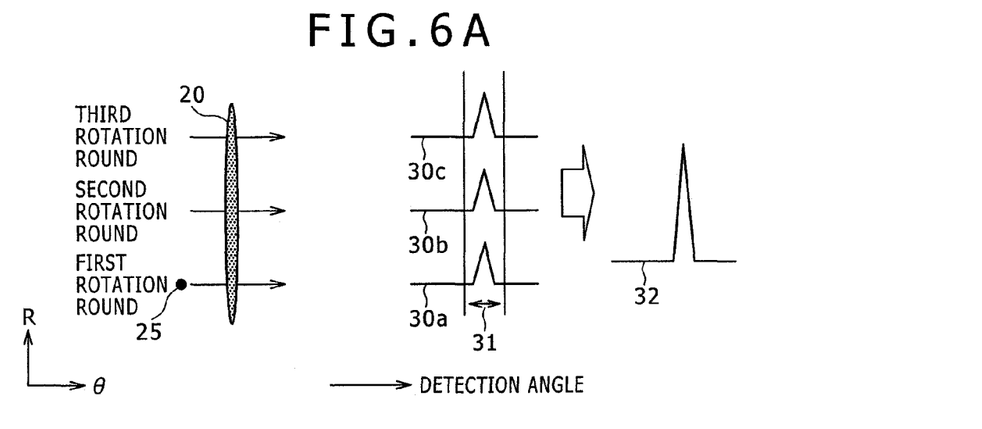
FIGS. 6A-6C are explanatory diagrams about operations such as addition and errors of detection timings of a plurality of scattered light rays.
Figure 6B:
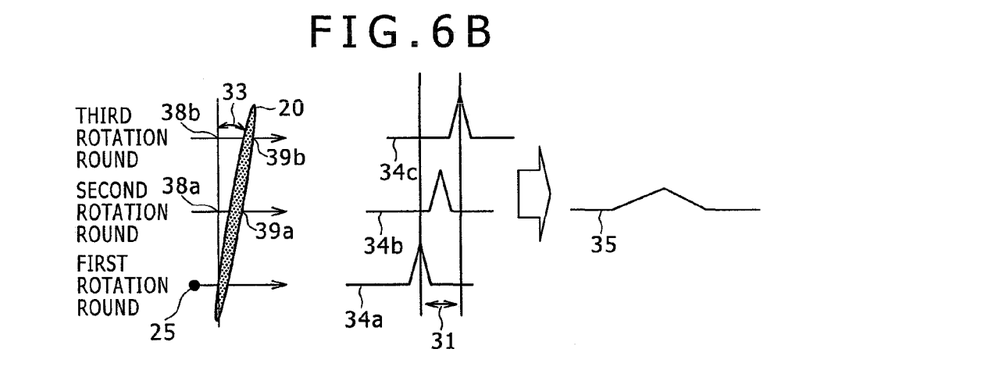
Figure 6C:
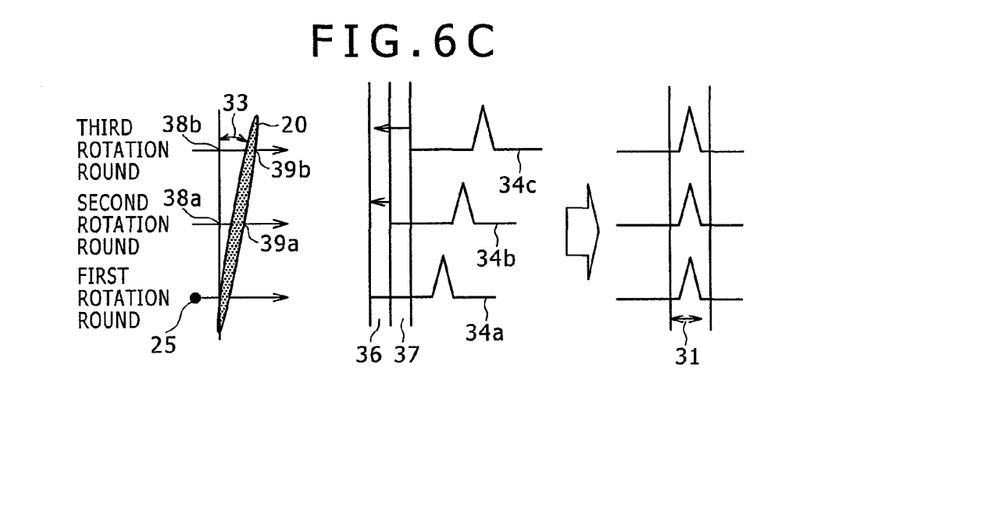

In the foregoing, the explanation about the apparatus and method for conducting irradiation on approximately the same area of the sample surface was given. However, a plurality of scattered light rays in approximately the same area may have errors of detection timings due to inclination of the illumination apparatus, the sensor, etc. Next, this error of the detection timing will be explained using FIG. 6A. A case where the defect 25 is illuminated three times in the illumination field 20 is considered. From a first rotation round, a detection signal 30*a* is obtained from the defect 25; from a second rotation round, a detection signal 30*b* is obtained; and from a third rotation round, a detection signal 30*c* is obtained, respectively. When the scattered light rays of the defect of the detection signals 30*a*, 30*b*, and 30*c* are detected at timing 31, it is possible to add them with excellent accuracy like a detection signal 32; therefore, it is possible to improve the detection sensitivity. However, when an angle 33 (hereinafter, written as an angle shift) of the longitudinal direction of the illumination field and the translation direction of the stage by the illumination apparatus and the sensor having inclinations is large, an error will arise between detection positions 38a, 38b corresponding to a detection angle that is a rotation angle of the sample controlled by the stage controller and irradiation positions 39a, 39b of the sample by the laser beam, which consequently will cause an error in detection timings of a plurality of scattered light rays by the same defect, like detection signals 34a, 34b, and 34c of FIGS. 6B and 6C. Therefore, since the scattered light from the same defect is not detected within the timing 31, the detected light cannot be added accurately and improvement of the detection sensitivity becomes difficult as a detection signal 35. That is, in order to add a plurality of scattered light rays with excellent accuracy, it is necessary to detect the scattered light rays of the same defect approximately at the same timing and to perform addition approximately at the same timing. For this purpose, a mechanism of monitoring and adjusting the illumination position, the angle shift, sensor inclination is needed and it is necessary to adjust timings 36, 37 of addition start of the plurality of detection signals. Below, an explanation will be given about a calibration method and an apparatus for calibrating the parameters in order to correct errors of detection timings that a plurality of scattered light rays have from approximately the same area in the present invention.

Figure 7:
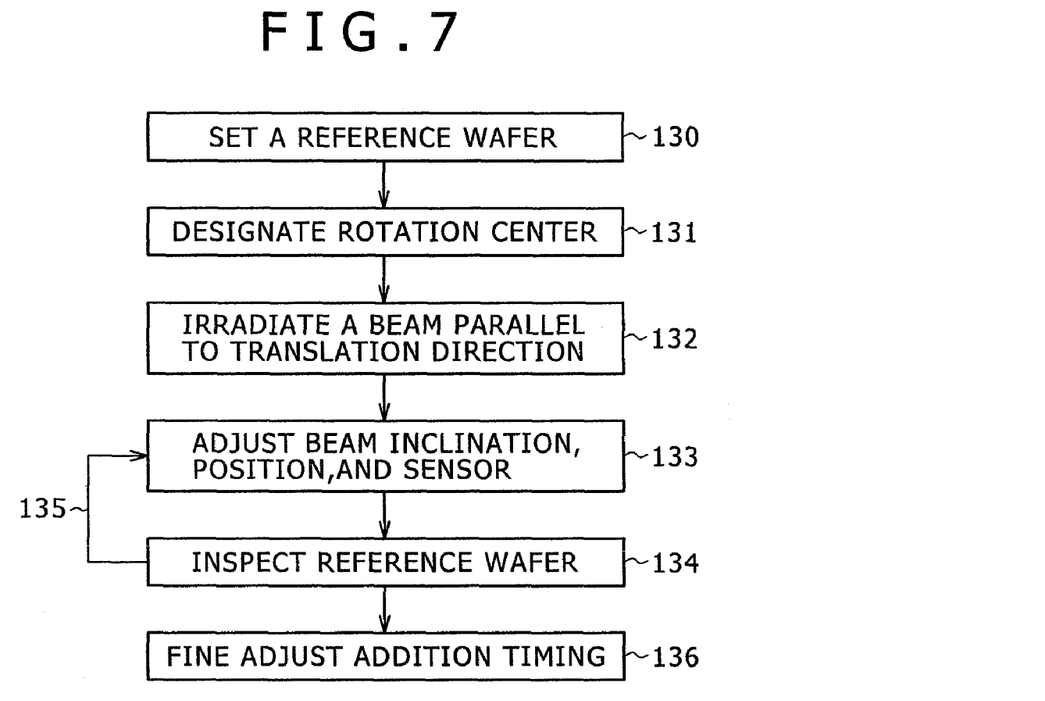
FIG. 7 is a flowchart about a calibration method.

FIG. 7 shows a flow of calibration. A reference wafer having a reference point at which a defect such as PSL is formed, its position being known, is set in the stage (Step 130). The wafer is rotated while being observed with the image formation optical system 12 and the CCD camera 13 in FIG. 1, and the rotation center of the stage is designated based on an amount of movement of the defect position (reference point). Illumination is conducted in a direction that passes through the rotation center and is approximately parallel to the translation direction of the stage (Step 132). The illumination position and the angle shift are adjusted while the defect position is being observed with the image formation optical system 12 and the CCD camera 13, and a geometrical relation between the illumination field and the detection range is adjusted by changing a sensor angle (Step 133). The same defect is measured using the reference wafer that was used at Step 130, and the detection timing is monitored (Step 134). Step 133 and Step 134 are repeated, and the timings at which the same defect is detected a plurality of times are made concordant with each other (Step 135). An error of the detection timing that cannot be corrected by a physical adjustment mechanism is adjusted by the signal processing section (Step 136).

Figure 8:
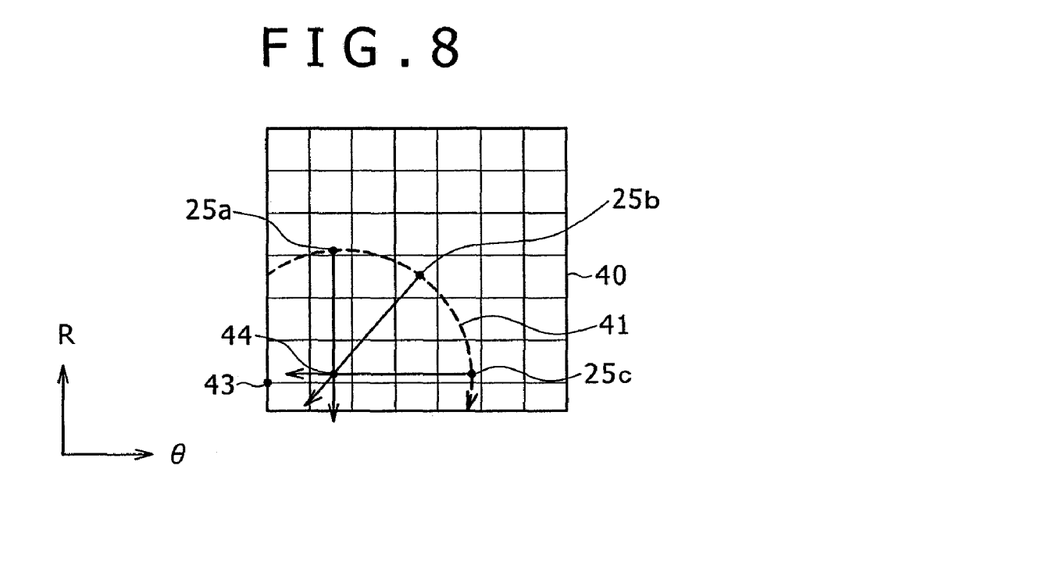
FIG. 8 is an explanatory diagram about a method for designating a stage rotation center.

Below, detailed explanation will be given for Step 130 to Step 136. Steps 130 and 131 will be explained using FIG. 8. FIG. 8 shows an explanation about a method for designating the rotation center of the stage. The reference wafer on which PSL is applied near the wafer center is set to the stage, and the stage is moved so that a central part of the wafer approximately comes in a view field with the CCD camera. A defect that is processed by FIB or the like may be used, even if it is not a PSL. It is desirable that the reference wafer is a wafer having large surface roughness. This is because of a reason that will be described later, namely, this is intended to monitor the illumination position by detecting the scattered light due to the surface roughness. If a defect enters in the view field, an image is tried to be acquired while the stage is being rotated. A case where the defect is detected in three images when the rotation causes positions of the defect to be changed is considered. In a detection range 40 of the CCD, the defects are detected at positions 25a, 25b, and 25c. Since the stage is rotating, the positions 25a, 25b, and 25c draw a circular arc 41. If an arbitrary pixel 43 on the CCD is set to an origin, coordinates of the positions 25a, 25b, and 25c are defined. If there are minimum three points, it is possible to compute rotation center coordinates 44 of the stage. When the curvature of the circular arch 41 is large, the view field is brought close to the rotation center and the above-mentioned procedure is performed again with the PSL nearer the rotation center. Although the explanation was given this time for the case where the three defects were detected, computation may be performed from more defect positions. Such a procedure gives an effect of improving coordinate accuracy of the rotation center.

Figure 9:
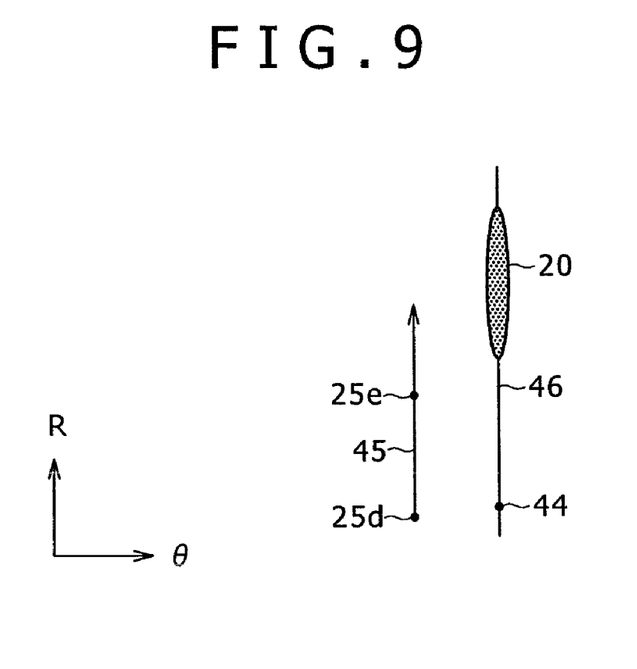
FIG. 9 is an explanatory diagram about a method for deciding an irradiation position and its direction.

FIG. 9 will explain Step 132. FIG. 9 illustrates a method for conducting the illumination in a direction that passes through the stage rotation center and is approximately parallel to the translation direction (R direction) of the stage. A case where a defect 25d exists in the vicinity of the rotation center 44 is considered. When the stage is translated, since the defect position (reference point) moves from the point 25d to a point 25e, it is possible to compute a translation direction 45 of the stage from the coordinates. Illumination is conducted on a direction 46 that passes through the rotation center 44 and is parallel to the translation direction 45.

Figure 10:
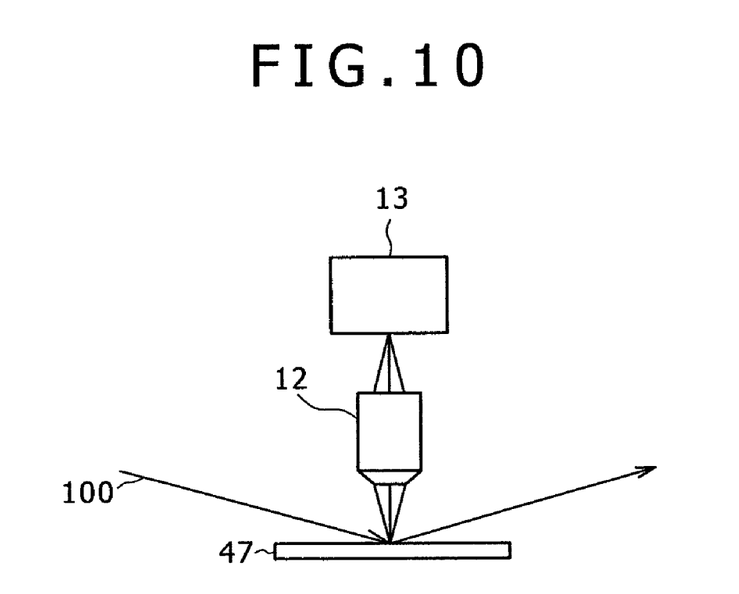
FIG. 10 is an explanatory diagram about a method for monitoring an illumination position.
Figure 11A:
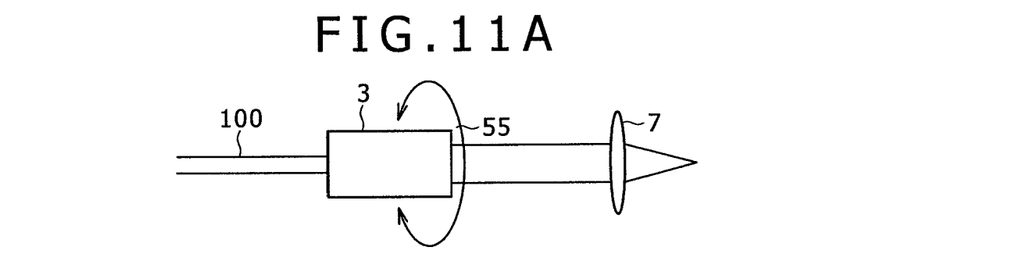
FIGS. 11A-11B are explanatory diagrams about a method for correcting an inclination of illumination on a wafer.
Figure 11B:
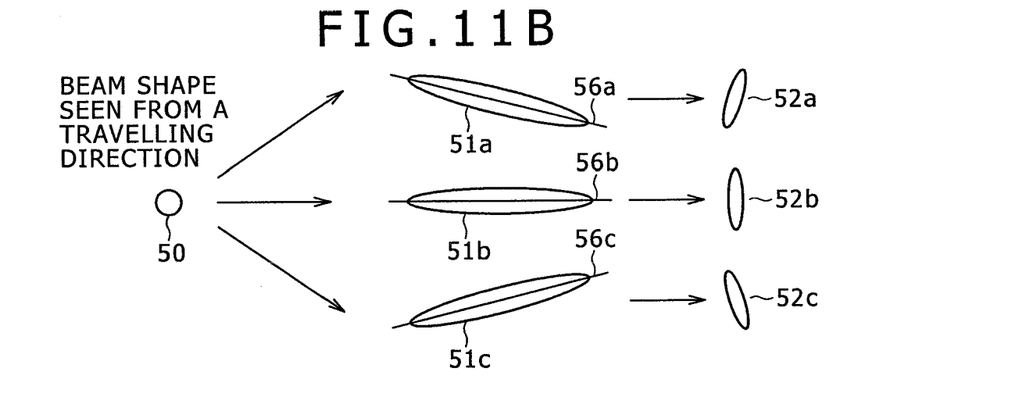

Next, Step 133 will be explained. FIG. 10 is an explanation of the method for monitoring the illumination position. Since a reference wafer 47 is a wafer having large surface roughness, which was described in the explanation of Steps 130, 131, the scattered light occurs much from surface unevenness. That is, the scattered light occurs from an area where illumination is conducted, and it is possible to designate the illumination position by monitoring the scattered light with the CCD 13. A method for correcting the angle shift will be explained using FIGS. 11A and 11B. FIG. 11A shows portions of the laser beam 100, the beam expander 3, and the collective lens 7 extracted from the illumination optical system. Just before entering into the expander, the laser beam has a shape of an almost complete circle 50 when viewed from its traveling direction. If after passing through the expander, magnification is changed in a direction 56b, it becomes of a beam shape like 51B. Then, the laser beam is reduced in the same direction as the direction 56b with the collective lens 7, and the illumination is conducted with the form 52b on the wafer. The expander 13 is rotatable in a plane 55 that is perpendicular to a laser traveling direction, which enables a beam shape irradiated on the wafer to be adjusted. Since a direction in which the magnification after passing through the expander changes can be altered as enlarged directions 56a, 56c by changing an angle of the expander, and thereby beam shapes like 51a, 51c are obtained, the illumination shape on the wafer can be adjusted like 52a, 52c. Since the laser traveling direction does not change by this adjustment, the irradiation position doe not change and the angle shift can be corrected in a plane perpendicular to the optical axis. The method for correcting the irradiation position can perform adjustment by changing tilt angles of the mirrors 5, 6 in FIG. 1.

Figure 12:
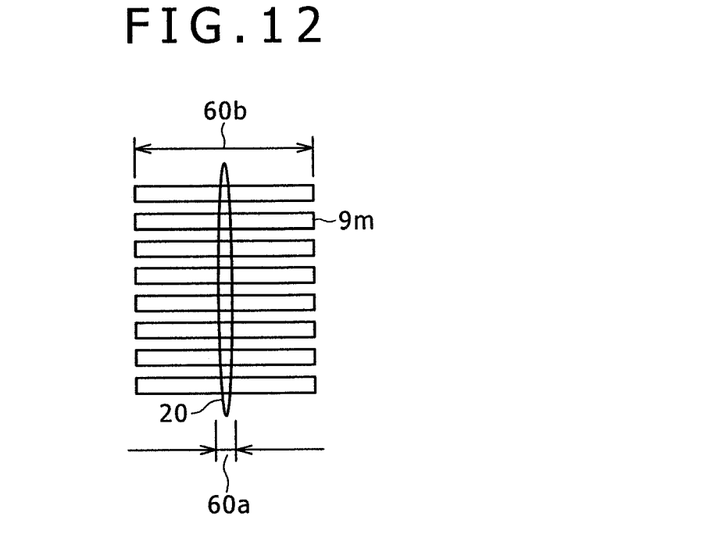
FIG. 12 is an explanatory diagram about a sensor whose sensor light receiving part is high, and the illumination position and inclination.
Figure 13:
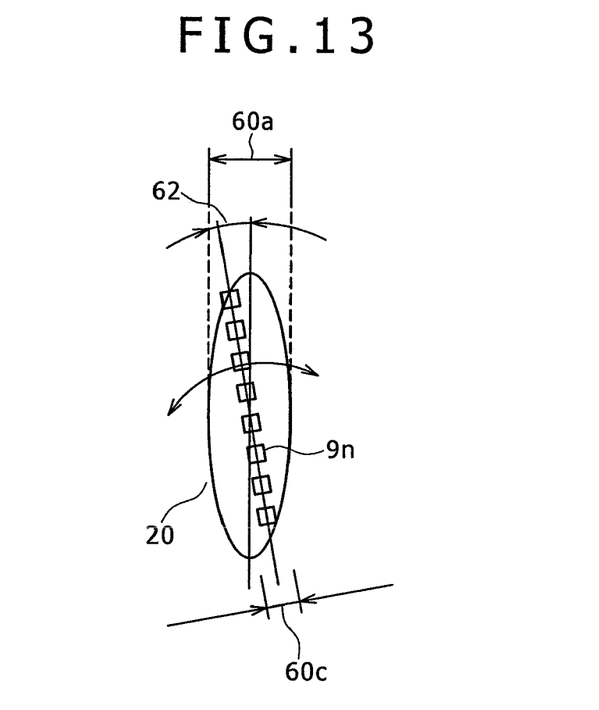
FIG. 13 is an explanatory diagram about a sensor whose sensor light receiving part is low, and the illumination position and inclination.

Correction of the inclination shift of a sensor plane with respect to the illumination position will be explained using FIGS. 12, 13. In the case of using a sensor 9m whose sensor light receiving part height 60b is large as compared to a widthwise direction 60a of an illumination range like FIG. 12, since the detection timing of the defect scattered light depends on the illumination position, if the angle shift is corrected with the above-mentioned technique, it becomes possible to correct the detection timing of the defect scattered light. In the case of using a sensor 9n whose sensor light receiving part height 60c is small as compared to the widthwise direction 60a of the illumination range, since the detection timing of the defect scattered light depends on the position of the sensor light receiving part, the detection timing is adjusted by adjusting an angle 62 with a fine movement rotation stage etc.

Figure 14:
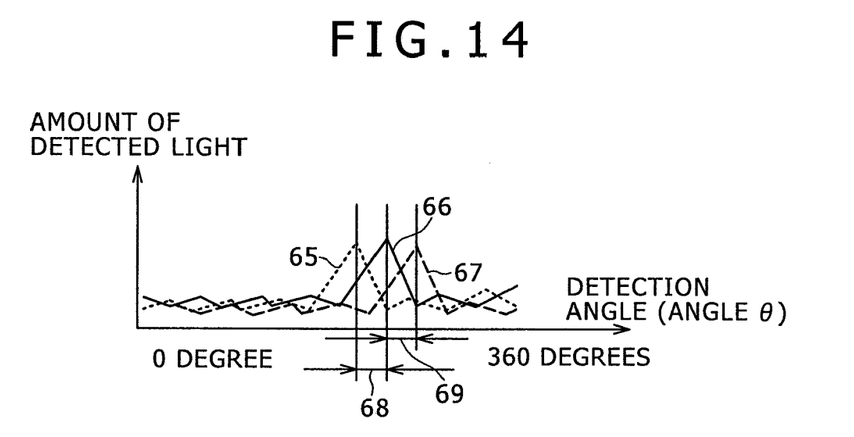
FIG. 14 is an explanatory diagram about the errors of the detection timings of the plurality of scattered light rays.

Step 134 and 135 will be explained by FIG. 14. FIG. 14 illustrates an explanation of a method for actually performing the inspection using the reference wafer having a reference point that is a defect whose position is known.

In FIG. 14, the horizontal axis denotes angle θ and the vertical axis denotes the amount of detected light, and FIG. 14 shows a relation of the amount of detected light and the angle θ when the same defect is detected a plurality of times. If the encoder pulses give a count of n pulses for one rotation, the encoder pulses 1st to n-th are included in the first rotation round, (n+1)-th to 2n-th are included in the second rotation round, (2n+1)-th to 3n-th are included in the third rotation round, and 1st pulse, (n+1)-th pulse, and (2n+1)-th pulse are shown as angle θ=0 degree. Considered is a case where the same defect is inspected, a detection signal like a signal 65 is obtained in the first rotation round, and a detection signal 66 in the second rotation round and a detection signal 67 in the third rotation round are obtained. A pulse shift 68 exists between the detection timing of the first rotation round and the detection timing of the second rotation round of the same defect, and a pulse shift 69 exists between the detection timing of the second rotation round and the detection timing of the third rotation round thereof. The timing shift is produced in response to the angle shift and the magnitude of inclination of the sensor, and the magnitudes of the shifts of the defect detection timings 68, 69 are almost comparable. Since one pulse of the encoder is equivalent to an angle of about several seconds or so, Step 133 and Step 134 are repeated until the detection timing shift becomes about over ten pulses.

Figure 15A:
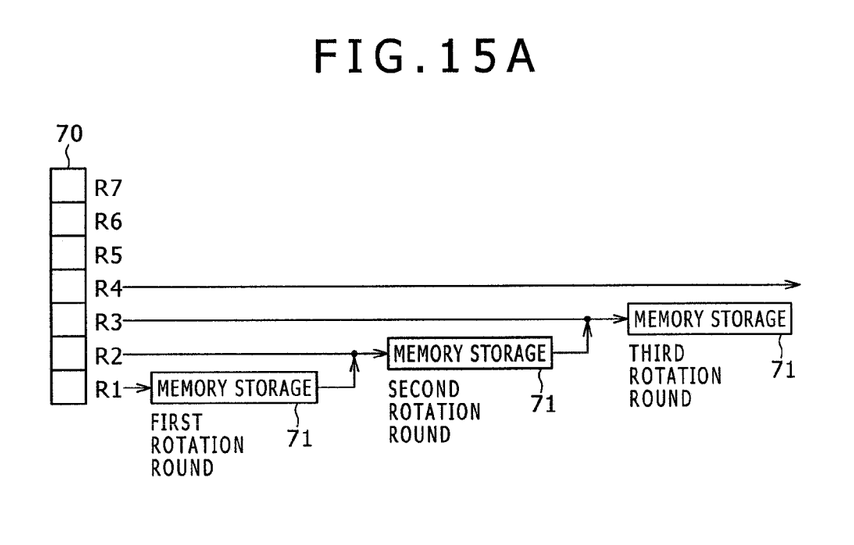
FIGS. 15A-15C are explanatory diagrams of a correction method of the errors of the detection timings.
Figure 15B:
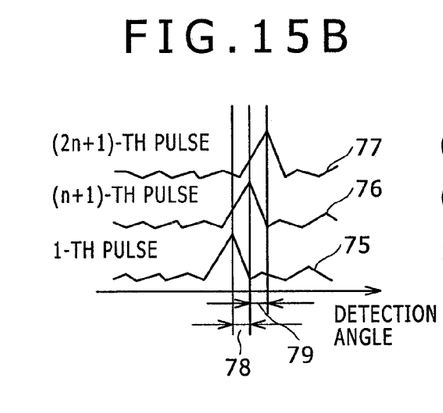
Figure 15C:
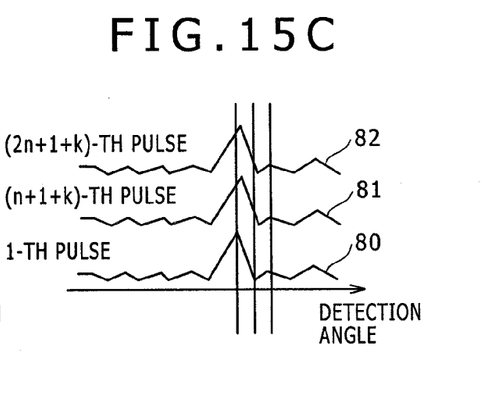

Step 136 will be explained using FIG. 15. In FIG. 15A, an addition method of the scattered light rays in a memory section will be described. A case where a sensor 70 detects the same defect three times is considered. Symbols R1 to R7 denote sensor light receiving parts, respectively. In the first rotation round, the detection signal of the light receiving part R1 of the sensor 70 is stored in memory 71 for the amount of light corresponding to one rotation, in the second rotation round, the detection signal of the light receiving part R2 is stored in the memory 71, and in the third rotation round, the detection signal of the light receiving part is stored in the memory 71. If the detection timing of the defect has a shift, a detection signal 75 is obtained in the first rotation round, a detection signal 76 is obtained in the second rotation round, and a detection signal 77 is obtained in the third rotation round, as shown in FIG. 15B. Therefore, it is difficult to perform addition with high accuracy. Even when the correction is performed in the steps 134, 135, it is actually difficult to make the detection signals agree with each other without an error as small as one pulse of the encoder due to mechanical precision, and consequently pulse shifts 78, 79 among the detection signals 75 to 77 exist. A case where the pulse shifts 78, 79 are comparable numbers of pulses that make a shift of k pulses is considered. If the detection signals of the first rotation round are specified to be encoder pulse 1 to (n+k), and the detection signals are stored in the memory 71, the storage start pulse of the second rotation round is specified as (n+1+k), and the storage start pulse of the third rotation round is specified as (2n+1+2k), it becomes possible to correct the detection signals so that the defect scattered light rays can be detected at approximately the same timing as shown in FIG. 15C, which goes with a detection signal 80 for the first rotation round, a detection signal 81 for the second rotation round, and a detection signal 82 for the third rotation round. Therefore, it becomes possible to add the scattered light signals of the same defect at approximately the same timing. Actually, there is a possibility that the pulse shifts 78, 79 have different number of pulses. In that case, what is necessary is just to find an average value together with the pulses 78, 79, and to designate the value as a k value and then perform the above-mentioned correction. Alternatively, it is all right to set a median of a plurality of pulse shifts as the k value and perform the correction. In the case where the median is used, when the plurality of pulse shifts include outliers, the k value can be obtained that is not affected largely by the outliers. Alternatively, it may be all right to set a difference of two pulse shifts to the k value and perform the correction. When the plurality of pulse shifts are comparable values, a value comparable to the k value computed by averaging can be obtained. Moreover, the correction of errors of detection timings that a plurality of scattered light rays from approximately the same area have may be performed using the k value being set up in advance using the reference wafer. In this case, it is not necessary to compute the k value for each sample that undergoes the defect inspection, reduction of a throughput can be prevented. Further, the k value may be computed sequentially using a sample having a reference point that is a defect whose position is known on the sample surface instead of the reference wafer, and the correction may be performed. In this case, since the detection timing can be corrected after finding the k value for each sample, a higher-precision addition result can be obtained.

Figure 16:
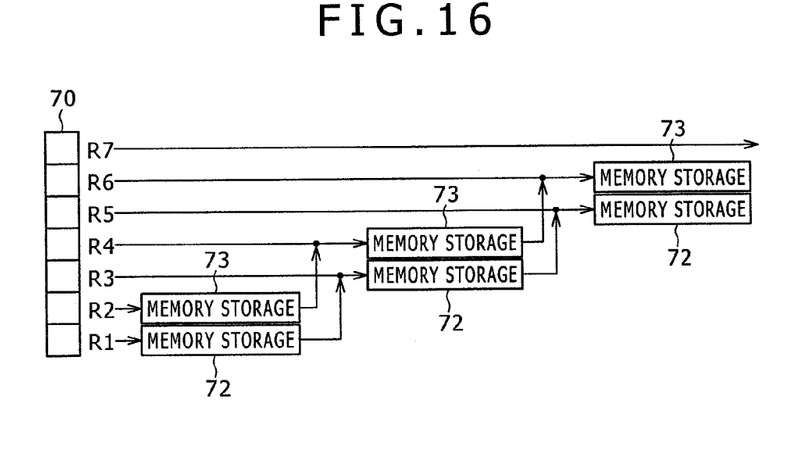
FIG. 16 is an explanatory diagram of a switch method of storage memory.

Next, a method for switching memory that stores detection signals will be explained. Although in the explanation in the above-mentioned FIG. 15, memory storing the detection signals is switched for each one of light receiving parts, the storage memory may be switched for each two of the light receiving parts as shown in FIG. 16. In the first rotation round, the detection signals of the light receiving part R1 are stored in memory 72; in the second rotation round, the detection signals of the light receiving part R3 are stored in the memory 72; and in the third rotation round, the detection signals of the light receiving part R5 are stored in the memory 72. Moreover, in the first rotation round, the detection signals of the light receiving part R2 are stored in memory 73; in the second rotation round, the detection signals of the light receiving part R4 are stored in the memory 73; and in the third rotation round, the detection signals of the light receiving part R6 are stored in the memory 73. Since by configuring the light receiving part as described above, an area that can be inspected in a single rotation becomes doubled, it becomes possible to double the feed pitch, and consequently the throughput can be improved. Although the explanation was given for the example where the storage memory is switched for every two light receiving parts, the number of switchover does not need to be two times and it is possible to enlarge the feed pitch further.

Figure 17:
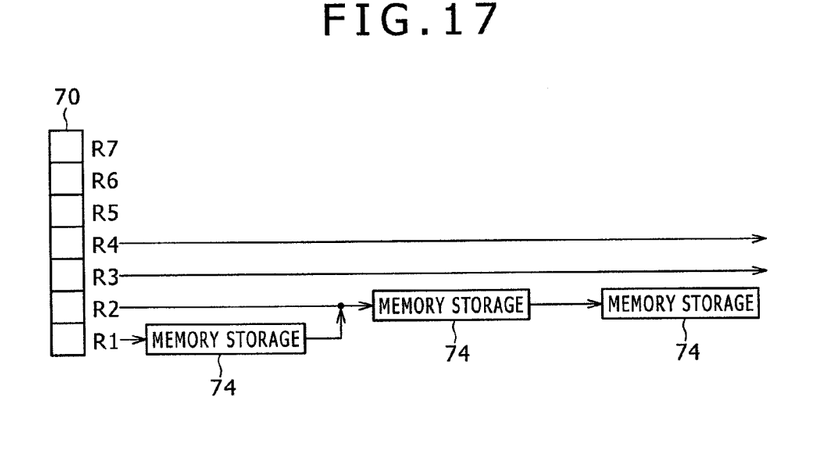
FIG. 17 is an explanatory diagram of the switch method of the storage memory in a wafer outermost peripheral part.

Next, the inspection method in the wafer peripheral part will be explained. In the conventional technology, scanning is performed spirally, and when the illumination field reaches an outermost peripheral part, the inspection will be completed. In the present invention, the method and the apparatus according to the present invention may be such that, when the illumination field reaches the outermost peripheral part, the stage movement to the radial direction is stopped, rotational scanning is concentrically performed, and the detection signal of the next one rotation is stored in the same memory without switching the storage memory of the detection signal. FIG. 17 explains a method for changing the storage memory in the case where the illumination field end reaches the outermost peripheral part at a time when the second rotation round completed and the rotational scanning is being performed concentrically in the third rotation round. In the first rotation round, the detection signal of the light receiving part R1 is stored in memory 74; in the second rotation round, the detection signal of the light receiving part R2 is stored in the memory 74; and in the third rotation round, the detection signal of the light receiving part R2 is stored in the memory 74. This scheme makes it possible to increase the number of additions in the outermost peripheral part. Here, since the concentric scanning is performed in an outer peripheral part, it is possible to freely set up the number of additions. In an inner peripheral part, a relation between the illumination field length and the feed pitch length decides the number of times of illumination being able to illuminate approximately the same area. However, the number of times of illumination in the outer peripheral part does not need to be equal to the number of times of illumination in the inner peripheral part, and it poses no problem even if that number is made larger than the number of times of illumination in the inner peripheral part.

Next, one example of the inspection method of the present invention will be explained. In the conventional technology, since linear velocity is slow in the sample inner peripheral part and the linear velocity becomes fast in the sample outer peripheral part; in the outer peripheral part, an irradiation time of the laser beam becomes short, and the detection sensitivity falls. In the present invention, it is possible to freely alter the number of additions even during a one-time inspection. It is possible to set up the number of additions arbitrarily by switching the feed pitch and the storage memory, for example, in this way: the number of additions is set to one time in an area from the rotation center to 50 mm or less, the number of additions is set to two times in an area within 100 mm, and the number of additions is set to three times in an area 101 mm or more. By this setup, it becomes possible to prevent the sensitivity from falling in the sample outer peripheral part, and to keep the detection sensitivity constant on the whole sample surface.

In the foregoing, the invention made by the present inventors was explained concretely based on the embodiment. However, it is needless to say that the present invention is not restricted to the above-mentioned embodiment but can be altered variously without departing from the spirit and scope of the present invention. Incidentally, although a plurality of scattered light rays from approximately the same area are added to perform defect detection, at this time, the plurality of scattered light rays may be averaged, not performing addition, to detect the defect. Moreover, the defect inspection apparatus may be equipped with a mechanism that enables the number of irradiation on approximately the same area to be set up freely by adjusting the length of the illumination field of the illumination, the translation speed of the stage, or the like according to a characteristic of an object under inspection etc. As described above, according to the embodiment of the present invention, the detection sensitivity can be improved by illuminating the same defect a plurality of times in a single inspection, correcting the errors of the detection timings that a plurality of scattered light rays occurring by it have, and then adding them. Moreover, the inspection can be performed without losing the throughput by using the photodiode array having a plurality of pixels. According to the embodiment of the present invention, it is possible to calibrate addition timings of a plurality of scattered light rays, and therefore it becomes possible to obtain a high-accuracy addition result. Moreover, it becomes possible to freely set up the number of additions according to an inspection area and inspection mode by using an addition timing correction function.

According to the present invention, the defect inspection method and the defect inspection apparatus that are capable of inspecting a minute defect existing on the sample surface with high sensitivity while suppressing damage to the sample can be provided.

The invention may be embodied in other specific forms without departing from the spirit or essential characteristics thereof. The present embodiment is therefore to considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A method for inspecting a defect of a surface of a sample, comprising the steps of:
    irradiating a laser beam on a sample surface so that at least a part of an illumination field of the laser beam illuminates a first area of the sample surface;
    detecting a plurality of scattered light rays from the first area caused by the irradiation in the irradiating step;
    correcting detection timing errors of inclination of an illumination apparatus and a sensor for the plurality of scattered light rays detected in the detecting step;
    at least one of adding and averaging the plurality of scattered light rays corrected in the correcting step; and
    determining a defect on the sample surface based on the plurality of scattered light rays in accordance with the correcting of the detection timing errors of inclination of the illumination apparatus and the sensor.

2. The defect inspection method according to claim 1, wherein in the step of correcting detection timing errors, the correction is performed using a detection timing error value that is determined using a reference wafer having a reference point which is a position of a known defect.

3. The defect inspection method according to claim 1, wherein in the step of correcting detection timing errors, the correction is performed using a detection timing error value that is determined using a position of a known defect on the sample surface.

4. The defect inspection method according to claim 1, wherein in the step of irradiating, the laser beam is irradiated so that the illumination field on the sample surface is a line.

5. The defect inspection method according to claim 1, wherein in the step of irradiating, a plurality of sub-laser beams which are divided from the laser beam are aligned and are made to irradiate the sample surface.

6. The defect inspection method according to claim 1, wherein a number of times of the at least one of adding or averaging are changed in accordance with a distance from a center of the sample surface.

7. The defect inspection method according to claim 1, further comprising the step of moving a stage which holds a sample in a radial direction and in a rotational direction so that a feed pitch which is a distance that the stage moves in the radial direction at a time point of the stage having made approximately one rotation is shorter than a length of the illumination field of the laser beam.

8. The defect inspection method according to claim 1, wherein the step of correcting detection timing errors includes a first correction step of correcting errors of detection timings by using physical adjustment, and a second correction step of correcting errors of detection timings by using signal processing adjustment.

9. The defect inspection method according to claim 8, wherein the second correction step is performed using pulse shift of detection signals based on the plurality of scattered light rays.

10. An apparatus for inspecting a defect of a surface of a sample, comprising:
- an irradiation unit for irradiating a laser beam on a sample surface so that at least a part of an illumination field of the laser beam illuminates a first area of the sample surface;
- a detection unit for detecting a plurality of scattered light rays from the first area caused by the irradiation unit; and
- a signal processing unit configured to correct detection timing errors of inclination of an illumination apparatus and a sensor for the plurality of scattered light rays detected in the detection unit, to at least one of add and average the plurality of scattered light rays which have been corrected, and to determine a defect on the sample surface based on the plurality of scattered light rays in accordance with the corrected detection timing errors of inclination of the illumination apparatus and the sensor.

11. The defect inspection apparatus according to claim 10, wherein the signal processing unit corrects detection timing errors using a detection timing error value that is determined using a reference wafer having a reference point which is a position of a known defect.

12. The defect inspection apparatus according to claim 10, wherein the signal processing unit corrects detection timing errors using a detection timing error value that is determined using a position of a known defect on the sample surface.

13. The defect inspection apparatus according to claim 12, further comprising a movement unit for moving a stage which holds a sample in a radial direction and in a rotational direction so that a feed pitch which is a distance that the stage moves in the radial direction at a time point of the stage having made approximately one rotation is shorter than a length of the illumination field of the laser beam.

* * * * *